(12) United States Patent
Tano et al.

(10) Patent No.: US 9,700,702 B2
(45) Date of Patent: Jul. 11, 2017

(54) GUIDE WIRE

(71) Applicant: TERUMO KABUSHIKI KAISHA, Shibuya-ku (JP)

(72) Inventors: Yutaka Tano, Shizuoka (JP); Yousuke Nabeshima, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 560 days.

(21) Appl. No.: 14/298,242

(22) Filed: Jun. 6, 2014

(65) Prior Publication Data

US 2014/0288533 A1 Sep. 25, 2014

Related U.S. Application Data

(63) Continuation of application No. PCT/JP2012/083854, filed on Dec. 27, 2012.

(30) Foreign Application Priority Data

Dec. 28, 2011 (JP) ................................. 2011-289187

(51) Int. Cl.
*A61M 25/09* (2006.01)

(52) U.S. Cl.
CPC ... *A61M 25/09* (2013.01); *A61M 2025/09091* (2013.01); *A61M 2025/09108* (2013.01);
(Continued)

(58) Field of Classification Search
CPC ........ A61M 25/09; A61M 2025/09133; A61M 2025/09091; A61M 2025/09108; A61M 2025/09175
(Continued)

(56) References Cited

U.S. PATENT DOCUMENTS

| 6,139,511 A | 10/2000 | Huter et al. |
| 2002/0010420 A1 | 1/2002 | Bagaoisan et al. |

(Continued)

FOREIGN PATENT DOCUMENTS

| EP | 2 075 030 A1 | 7/2009 |
| JP | 2001-514544 A | 9/2001 |

(Continued)

OTHER PUBLICATIONS

WO 2011/118443A1, Nabeshima et al., date of publication: Sep. 29, 2011.*

(Continued)

*Primary Examiner* — Manuel Mendez
(74) *Attorney, Agent, or Firm* — Buchanan Ingersoll & Rooney PC

(57) ABSTRACT

A guide wire has a wire body; and a distal side coating layer that covers a distal portion of the wire body. The guide wire has a cylindrical member that has an outer diameter substantially the same as an outer diameter of a proximal portion of the distal side coating layer, that encircles a portion of the wire body and that has a distal portion positioned proximate the proximal portion of the distal side coating layer; and a joint member that is disposed at a proximal side of the cylindrical member and joins the cylindrical member and the wire body. The joint member has a gradually decreasing outer diameter portion whose outer diameter gradually decreases toward a proximal side of the wire body, and an outer peripheral surface of the cylindrical member has a surface continuous with the gradually decreasing outer diameter portion.

13 Claims, 3 Drawing Sheets

(52) U.S. Cl.
CPC ............ *A61M 2025/09133* (2013.01); *A61M 2025/09175* (2013.01)

(58) Field of Classification Search
USPC ................. 604/96.01, 523–536; 600/585
See application file for complete search history.

(56) References Cited

U.S. PATENT DOCUMENTS

| | | | |
|---|---|---|---|
| 2002/0095137 A1 | 7/2002 | Zadno-Azizi et al. | |
| 2002/0177800 A1 | 11/2002 | Bagaoisan et al. | |
| 2007/0255217 A1* | 11/2007 | Burkett ............ | A61B 17/12145 604/164.13 |
| 2008/0194992 A1 | 8/2008 | Satou et al. | |
| 2008/0281230 A1* | 11/2008 | Kinoshita ............ | A61M 25/09 600/585 |
| 2011/0319872 A1 | 12/2011 | Kawasaki | |
| 2013/0006222 A1 | 1/2013 | Nabeshima et al. | |

FOREIGN PATENT DOCUMENTS

| | | |
|---|---|---|
| JP | 2001-526559 A | 12/2001 |
| JP | 2008-307367 A | 12/2008 |
| JP | 2010-214054 A | 9/2010 |
| WO | WO 02/083229 A2 | 10/2002 |
| WO | WO 2011/118443 A1 | 9/2011 |

OTHER PUBLICATIONS

International Search Report (PCT/ISA/210) mailed on Mar. 12, 2013, by the Japanese Patent Office as the International Searching Authority for International Application No. PCT/JP2012/083854.

Office Action (Notice of Reasons for Rejection) issued on Jul. 19, 2016, by the Japanese Patent Office in Japanese Patent Application No. 2013-551789, and an English Translation of the Office Action. (6 pages).

Extended European Search Report dated Jul. 28, 2015, issued by the European Patent Office in the corresponding European Application No. 12863339.3. (8 pages).

Office Action (Notification of the First Office Action) issued on Nov. 2, 2015, by the Patent Office of the People's Republic of China in corresponding Chinese Application No. 2012800651001, and an English translation of the Office Action. (13 pages).

Office Action (Second) issued on May 6, 2016, by the Patent Office of the People's Republic of China in corresponding Chinese Patent Application No. 2012800651001 and an English translation of the Office Action. (10 pgs).

* cited by examiner

ID WIRE

CROSS REFERENCES TO RELATED APPLICATIONS

This application is a continuation of International Application No. PCT/JP2012/083854 filed on Dec. 27, 2012, and claims priority to Japanese Application No. 2011-289187 filed on Dec. 28, 2011, the entire content of both of which are incorporated herein by reference.

TECHNICAL FIELD

The present disclosure relates to a guide wire.

BACKGROUND DISCUSSION

In order to guide a catheter to a target site of a living body lumen, such as a digestive tract or a blood vessel, a guide wire is used when inserting the catheter into the living body lumen. The guide wire is used in this manner in a position in which it is inserted into the catheter. For example, during observation or treatment of a target site using an endoscope inserted into a living body lumen, a guide wire is used in order to guide a catheter inserted into the endoscope or a lumen of the endoscope to the target site.

Known guide wires, such as disclosed in JP-A-2008-307367 and WO2011/118443, have an elongated wire body, a resin coating layer covering a distal portion of the wire body and an annular member arranged on a proximal side of the resin coating layer. In these guide wires, a proximal outer diameter of the resin coating layer and a distal outer diameter of the annular member are provided in order to help prevent turning up of the resin coating layer, but further measures to help prevent turning up of the resin coating layer are needed.

SUMMARY

The present application discloses a guide wire which can reliably prevent a medical device such as a catheter used in combination with the guide wire from being caught on a turned-up portion when a proximal side portion of a coating layer is turned up.

A guide wire according to this application includes an elongated wire body having flexibility; a distal side coating layer that covers a distal portion of the wire body and is made of a resin material; a cylindrical member that has an outer diameter substantially the same as an outer diameter of a proximal portion of the distal side coating layer, that encircles a portion of the wire body and that has a distal portion positioned proximate the proximal portion of the distal side coating layer; and a joint member that is disposed at a proximal side of the cylindrical member and joins the cylindrical member and the wire body, in which the joint member has a gradually decreasing outer diameter portion whose outer diameter gradually decreases toward a proximal side of the wire body, and an outer peripheral surface of the cylindrical member has a surface continuous with the gradually decreasing outer diameter portion.

In an embodiment, the joint member is made of a material softer than a material of the cylindrical member.

In an embodiment, a distal end of the cylindrical member is in contact with the proximal portion of the distal side coating layer.

In an embodiment, a proximal portion of the cylindrical member has a gradually decreasing outer diameter portion whose outer diameter gradually decreases toward the proximal side of the wire body, and an outer peripheral surface of the gradually decreasing outer diameter portion has a surface continuous with the gradually decreasing outer diameter portion of the joint member.

In an embodiment, the joint member is inserted from the proximal side of the cylindrical member into a portion between an outer peripheral surface of the wire body and an inner peripheral surface of the cylindrical member.

In an embodiment, the joint member is made of an adhesive or solder.

In an embodiment, a portion where the outer peripheral surface of the wire body is overlapped with the cylindrical member is processed so that wettability of the adhesive or the solder is higher than that of the other portions.

In an embodiment, the cylindrical member is made of a metal material.

A guide wire according to this application includes an elongated wire body having flexibility; a distal side coating layer that covers a distal portion of the wire body and is made of a resin material; a cylindrical member that has an outer diameter substantially the same as an outer diameter of a proximal portion of the distal side coating layer, that encircles a portion of the wire body and that has a distal portion positioned proximate the proximal portion of the distal side coating layer; and a joint member that is disposed at a proximal side of the cylindrical member and joins the cylindrical member and the wire body, in which the joint member has a gradually decreasing outer diameter portion whose outer diameter gradually decreases toward a proximal side of the wire body, and a proximal portion of the cylindrical member has a gradually decreasing outer diameter portion whose outer diameter gradually decreases toward the proximal side of the wire body.

When continuously pushing a medical device such as a catheter used in combination with a guide wire (referred to as a "catheter" as a representative example) to a target site of a living body lumen along the guide wire toward a distal direction, a distal end of the catheter slides on a surface continuous with an outer peripheral surface of a cylindrical member from a gradually decreasing outer diameter portion of a joining portion, and slides to a distal side coating layer which has substantially the same outer diameter. Therefore, it is possible to reliably prevent the distal of the catheter from being caught thereon.

DETAILED DESCRIPTION

Figure 1:
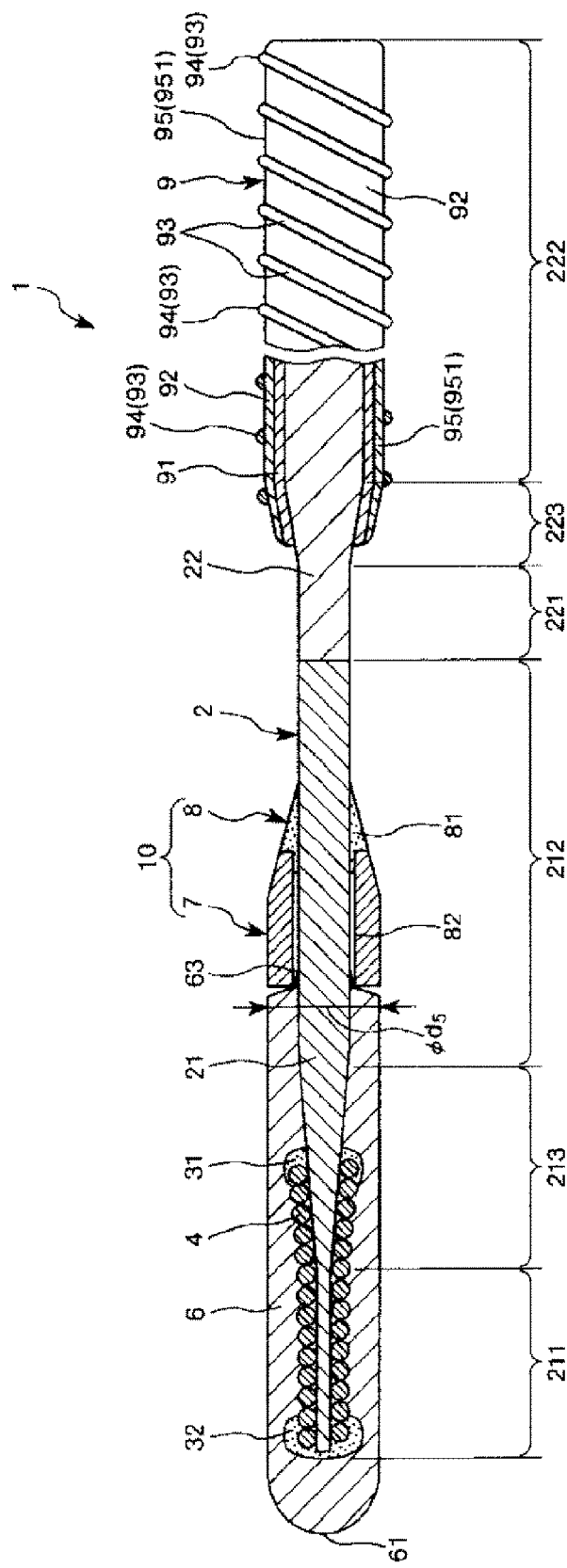
FIG. 1 is a vertical cross-sectional view illustrating an exemplary guide wire.

Hereinafter, a guide wire will be described in detail with reference to a preferred embodiment illustrated in the accompanying drawings. For convenience of description, a right side in the drawings is referred to as "proximal", and a left side in the drawings is referred to as "distal". In each drawing, in order to facilitate understanding, the guide wire is schematically illustrated in such a manner that the guide wire is shortened in a longitudinal direction and is excessively extended in a thickness direction. A ratio of dimensions in the longitudinal direction to dimensions in the thickness direction will differ in practice from the ratios depicted in the schematic illustrations.

Figure 2:
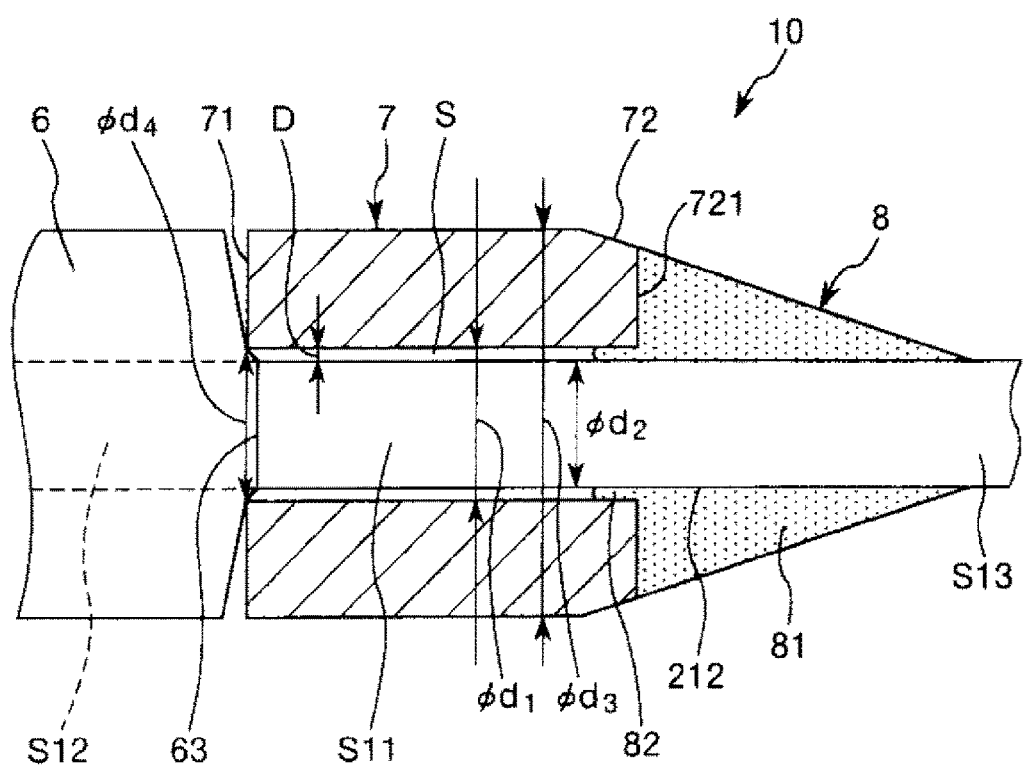
FIG. 2 is an enlarged cross-sectional view of a protruding portion included in the guide wire illustrated in FIG. 1.
Figure 3:
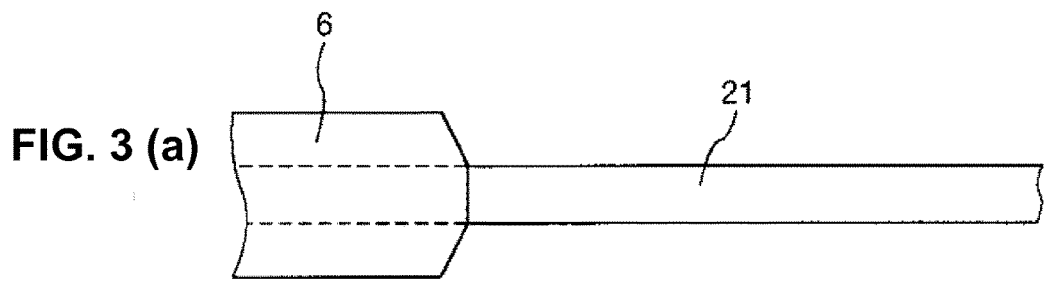
FIGS. 3(a), 3(b), 3(c), and 3(d) are cross-sectional views illustrating an example of a manufacturing method of the guide wire illustrated in FIG. 1.
Figure 3:
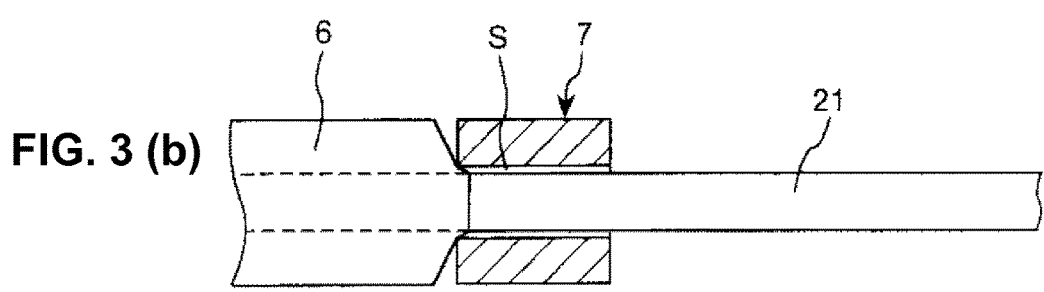
Figure 3:
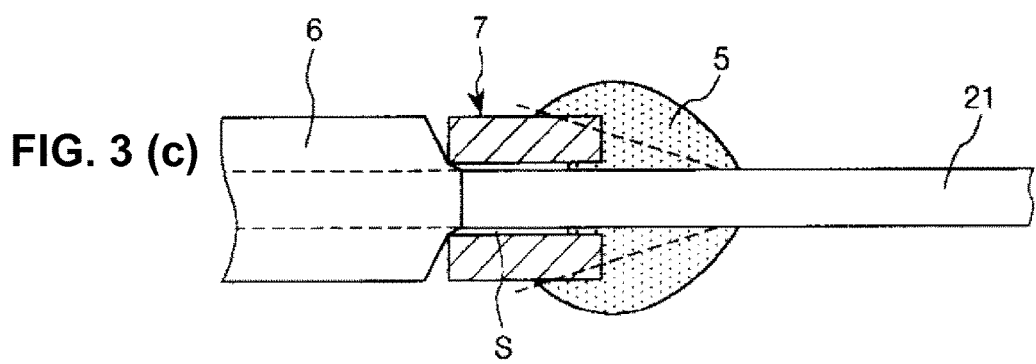
Figure 3:
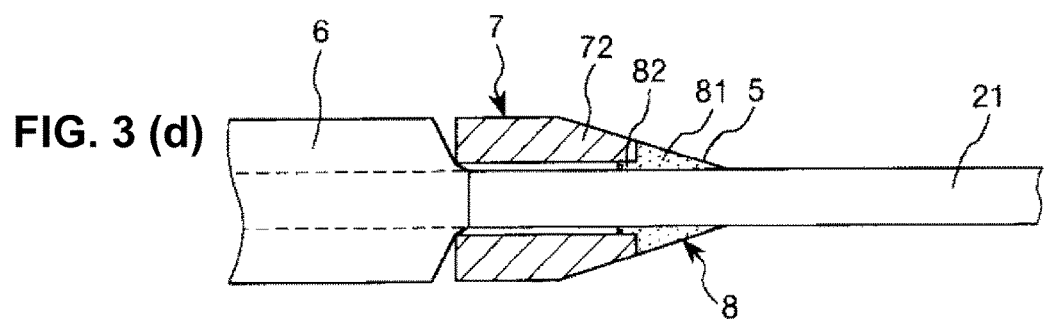

A guide wire 1 illustrated in FIGS. 1 to 3 is a catheter guide wire used by being inserted into a lumen of a catheter, which may be, for example, part of an endoscope. The guide wire 1 includes an elongated wire body 2, a spiral coil 4, a distal side coating layer 6 (hereinafter, referred to as a "resin coating layer 6"), a protruding portion 10 protruding from the wire body 2, and a proximal side coating layer 9. The protruding portion 10 is configured to have a cylindrical member 7 and a joint member 8.

An overall length of the guide wire 1 is not particularly limited, but it is preferable that the overall length be approximately 200 mm to 5,000 mm. An average outer diameter of the guide wire 1 is not particularly limited, but it is preferable that the average outer diameter be approximately 0.2 mm to 1.2 mm.

As illustrated in FIG. 1, the wire body 2 is configured to have a first wire 21 arranged at the distal side and a second wire 22 arranged at the proximal side of the first wire 21. The first wire 21 and the second wire 22 are firmly connected to each other, for example, by welding.

A welding method between the first wire 21 and the second wire 22 is not particularly limited. For example, the welding method can include spot welding using a laser, butt resistance welding such as butt seam welding, and the like. However, it is preferable to use butt resistance welding.

The first wire 21 and the second wire 22 may be joined together by being inserted into a tube shaped body in addition to being welded together. Alternatively, the wire body 2 may be configured as a single member.

The first wire 21 is a wire having elasticity. A length of the first wire 21 is not particularly limited, but it is preferable that the length be approximately 20 mm to 1,000 mm.

In the present embodiment, the first wire 21 has constant outer diameter portions 211 and 212 which are positioned in both end portions thereof and whose outer diameters are constant in the longitudinal direction, and a tapered portion (first gradually decreasing outer diameter portion) 213 which is positioned between the constant outer diameter portions 211 and 212 and whose outer diameter gradually decreases toward the distal side of the wire body 2.

By providing the tapered portion 213, it is possible to gradually decrease rigidity (flexural rigidity, torsional rigidity) of the first wire 21 toward the distal side of the wire body 2. As a result, the guide wire 1 can have excellent flexibility in the distal portion, thereby improving the ability to follow blood vessels and safety of the device during use. In addition, providing the tapered portion 2013 can help prevent the guide wire 1 from being bent during use.

The length of the tapered portion 213 is not particularly limited, but it is preferable that the length be approximately 10 mm to 1,000 mm, and it is more preferable that the length be approximately 20 mm to 300 mm. Providing for the length to fall within this range can make possible a more gradual change in rigidity along the longitudinal direction.

In the present embodiment, the tapered portion 213 has a tapered shape whose outer diameter continuously decreases toward the distal side of the wire body 2 at a substantially constant decreasing rate. In other words, a tapering angle of the tapered portion 213 is substantially constant along the longitudinal direction. This enables the guide wire 1 to more gradually change in rigidity along the longitudinal direction.

Unlike in the above-described configuration, the tapering angle of the tapered portion 213 may change along the longitudinal direction. For example, the tapered portion 213 may be formed by alternately repeating a relatively large tapering angle portion and a relatively small tapering angle portion multiple times. In this case, some portions of the tapered portion 213 may be formed so that the tapering angle is zero degrees.

It is preferable for a material of the first wire 21 to include a metal material. For example, it is possible to use various metal materials such as stainless steel (for example, SUS304, SUS303, SUS316, SUS316L, SUS316J1, SUS316J1L, SUS405, SUS430, SUS434, SUS444, SUS429, SUS430F, SUS302, and the like) and pseudo-elastic alloys (including super-elastic alloy). However, it is preferable to use a super-elastic alloy. Super-elastic alloys are relatively flexible, resilient, and unlikely to be curled. By making the first wire 21 from a material including a super-elastic alloy, the guide wire 1 can have sufficient flexibility and resilience against bending at a distal side portion thereof. Thus, it is possible to enhance operability by improving the ability to follow blood vessels which are complicatedly curved and bent such that, even if the first wire 21 is repeatedly curved and bent, the first wire 21 is unlikely to be curled by the resilience. Therefore, it is possible to avoid a degraded operability which may otherwise be caused by the first wire 21 being curled when the guide wire 1 is used.

The pseudo-elastic alloys referred to above include all of those which have any shape of stress-strain curves caused by tension, those which can significantly measure a transformation point of As, Af, Ms, Mf or the like, those which cannot measure the transformation point, and those which are largely deformed by stress and restore their own shape by removing the stress.

A preferred composition of super-elastic alloy includes Ni—Ti alloys such as Ni—Ti alloys containing Ni in a range of 49 at % to 52 at %, Cu—Zn alloys containing Zn in a range of 38.5 wt % to 41.5 wt %, Cu—Zn—X alloys containing X in a range of 1 wt % to 10 wt % (where X is at least one type among Be, Si, Sn, Al and Ga), Ni—Al alloys containing Al in a range of 36 at % to 38 at %, and the like. Among these, a particularly preferred composition is the aforesaid Ni—Ti alloy.

The distal portion of the second wire 22 is fixed with the proximal portion of the first wire 21. The second wire 22 is a wire having elasticity. The length of the second wire 22 is not particularly limited, but it is preferable that the length be approximately 20 mm to 4,800 mm.

In the present embodiment, the second wire 22 has constant outer diameter portions 221 and 222 which are positioned in both end portions thereof and whose outer diameters are constant in the longitudinal direction, and a tapered portion (second gradually decreasing outer diameter portion) 223 which is positioned between the constant outer diameter portions 221 and 222 and whose outer diameter gradually decreases toward the distal side of the wire body 2. In the embodiment, the outer diameter of the constant outer diameter portion 221 is substantially equal to the outer diameter of the constant outer diameter portion 212 of the first wire 21.

By disposing the tapered portion 223 in the second wire 22, it is possible to gradually decrease rigidity (flexural rigidity, torsional rigidity) of the second wire 22 toward the distal side of the wire body 2. As a result, operability and safety are improved when the guide wire 1 is inserted into a living body.

In the present embodiment, the tapered portion 223 has a tapered shape whose outer diameter continuously decreases toward the distal side of the wire body 2 at a substantially constant decreasing rate. In other words, a tapering angle of the tapered portion 223 is substantially constant along the longitudinal direction. This enables the guide wire 1 to more gradually change in rigidity along the longitudinal direction.

Unlike in the above-described configuration, the tapering angle of the tapered portion 223 may change along the longitudinal direction. For example, the tapered portion 223 may be formed by alternately repeating a relatively large tapering angle portion and a relatively small tapering angle portion multiple times. In this case, some portions of the tapered portion 223 may be formed so that the tapering angle is zero degrees.

It is preferable for a material of the second wire 22 to include a metal material. It is possible to use various metal materials such as stainless steel (for example, all types of SUS such as SUS304, SUS303, SUS316, SUS316L, SUS316J1, SUS316J1L, SUS405, SUS430, SUS434, SUS444, SUS429, SUS430F, SUS302, and the like), a piano wire, cobalt-based alloys, and pseudo-elastic alloys.

Among these, the cobalt-based alloys have a high elastic modulus when formed into the wire, and an appropriate elastic limit. Therefore, the second wire 22, when made with a cobalt-based alloy, can have a particularly excellent torque transmission capability, and thus undesirable buckling is extremely unlikely to occur. Any cobalt-based alloy containing Co as an element may be used. However, it is preferable to use those which contain Co as a main ingredient (i.e., an alloy in which, among elements making up the alloy, the Co content rate in terms of weight ratio is the highest). It is more preferable to use Co—Ni—Cr-based alloys, which have plasticity even in deformation at room temperature. Accordingly, for example, it is possible to easily deform the alloy into a desired shape when in use. In addition, such alloys have a high elastic modulus and can be subjected to cold forming with a high elastic limit. Since the alloy has to high elastic limit, it is possible to miniaturize the guide wire 1 while sufficiently preventing buckling from occurring. Therefore, it is possible to allow the guide wire 1 to have sufficient flexibility and rigidity for being inserted into a desired site. In addition, when stainless steel is used as a material of the second wire 22, the guide wire 1 can have improved thrust-in performance and torque transmission capability.

In the guide wire 1, the first wire 21 and the second wire 22 may be configured to have an alloy of the same type. The alloy may be a pseudo-elastic alloy, and for example, may include Ni—Ti-based alloys.

In the guide wire 1, the first wire 21 and the second wire 22 may be configured to have alloys which are different types from each other. In this case, it is preferable that the first wire 21 be made with a material having an elastic modulus lower than that of the second wire 22. This allows the guide wire 1 to have an excellent flexibility in the distal side portion and to have sufficient rigidity (flexural rigidity, torsional rigidity) in the proximal side portion. As a result, the guide wire 1 can have excellent thrust-in performance and torque transmission capability. And while ensuring a good operability, the guide wire 1 can have good flexibility and resilience in the distal side. In this regard, an ability to follow blood vessels and safety can be improved.

In a specific combination of the first wire 21 and the second wire 22, it is preferable that the first wire 21 be configured to have a super-elastic alloy (Ni—Ti alloy) and the second wire 22 be configured to have a stainless steel. This allows the above-described effects to be more conspicuous.

The coil 4 is arranged to extend around an outer periphery of the distal portion of the wire body 2. The coil 4 is a member formed by winding element wires in a spiral shape and covers the outer periphery of the distal portion of the wire body 2. The wire body 2 is inserted through a substantially central portion inside the coil 4. In the guide wire 1, the coil 4 is in contact with the wire body 2, that is, is in close contact with the outer periphery of the wire body 2. However, without being limited thereto, for example, the coil 4 may be separated from the outer periphery of the wire body 2.

In the guide wire 1, in a state in which no external force is received, the coil 4 has no gap between the element wires wound in the spiral shape as illustrated in FIG. 1. However, in an unillustrated embodiment, there may be a gap between the element wires wound in the spiral shape in a state in which no external force is received.

It is preferable that the coil 4 be configured to have an X-ray opaque metal material (material having an X-ray contrast property). For example, the material may include precious metals such as gold, platinum, tungsten and the like, or alloys containing these (for example, platinum-iridium alloy). When the coil 4 is configured to have the X-ray opaque metal material, the guide wire 1 has an X-ray contrast property. With such a configuration, it is possible to insert the guide wire 1 into the living body while checking a position of the distal portion in X-ray fluoroscopy.

The proximal portion of the coil 4 is fixed to the tapered portion 213 of the wire body 2 via a fixing material 31, and the distal portion of the coil 4 is fixed to the constant outer diameter portion 211 of the wire body 2 via a fixing material 32. The fixing materials 31 and 32 are respectively configured to have various adhesives or solder (brazing material).

The guide wire 1 has a resin coating layer 6 which collectively covers the distal portion of the wire body 2, the coil 4 and the fixing materials 31 and 32. The resin coating layer 6 is in close contact with the outer periphery of the distal portion of the wire body 2. In the present embodiment, the resin coating layer 6 is not inserted into the coil 4, but the resin coating layer 6 may be inserted into the coil 4 in an alternative embodiment.

The resin coating layer 6 can be provided for various purposes. For example, the resin coating layer 6 can be provided to improve an operability of the guide wire 1 by enhancing a sliding property, and to improve safety when inserting the guide wire 1 into a blood vessel.

The resin coating layer 6 is made from a sufficiently flexible material (soft material, elastic material). The material is not particularly limited, but for example, can include a polyolefin such as a polyethylene, a polypropylene and the like, a polyvinyl chloride, a polyester (PET, PBT and the like), a polyamide, a polyimide, a polyurethane, a polystyrene, a polycarbonate, a silicone resin, a fluorine resin (PTFE, ETFE, PFA and the like), or composite materials thereof, various rubber materials such as a latex rubber, a silicone rubber and the like, or composite materials obtained by combining two or more out of these materials. It is preferable to use a urethane-based resin out of these materials. If the resin coating layer 6 is mainly made from a urethane-based resin, flexibility in the distal portion of the guide wire 1 can be further improved such that, for example, when inserting the guide wire 1 into a blood vessel, it is possible to reliably prevent damage to the endothelial wall inside the blood vessel, thereby greatly improving safety.

A distal surface 61 of the resin coating layer 6 is rounded. This enables the distal surface 61 to help prevent damage to an endothelial wall of a body cavity such as a blood vessel. In addition, the proximal end 63 of the resin coating layer 6 is positioned in the constant outer diameter portion 212 of the wire body 2 (first wire 21).

Particles (filler) composed of the X-ray opaque material may be dispersed in the above-described resin coating layer 6. In this case, the guide wire 1 will have the X-ray contrast property. Therefore, it is possible to insert the guide wire 1 into the living body while checking a position of the distal portion in X-ray fluoroscopy. The X-ray opaque material is not particularly limited, but for example, includes precious metals such as platinum, tungsten and the like, or an alloy material containing these materials.

A thickness of the resin coating layer 6 is not particularly limited, but may be appropriately selected in view of the material and forming method of the resin coating layer 6. In general, the average thickness is preferably approximately 5 μm to 500 μm, and more preferably approximately 10 μm to 350 μm. In an embodiment, the resin coating layer 6 may be a laminated body having two or more layers.

The proximal side coating layer 9 is formed so as to cover the proximal portion of the wire body 2, specifically, substantially an entire region from the proximal portion of the second wire to the tapered portion 223. The proximal side coating layer 9 is configured so that an inner layer 91, an outer layer 92 and a linear body 93 are formed (stacked) around the outer periphery of the wire body 2 in this order.

The inner layer 91 is formed on the outer periphery of the wire body 2. The resin material of the inner layer 91 is not particularly limited, but it is preferable to use a fluorine-based resin material, for example. For example, the inner layer 91 can contain two types of fluorine-based resin material whose compositions are different from each other. As two types of fluorine-based resin material, it is possible to use polytetrafluoroethylene (PTFE) for one type and fluoride ethylene propylene (FEP) for the other type.

Furthermore, the inner layer 91 is formed on the outer periphery of the wire body 2. Therefore, for example, in order to improve the adhesion to the wire body 2, the inner layer 91 can contain a resin material functioning as a binder.

The thickness of the inner layer 91 is not particularly limited, but for example, it is preferable that the thickness be 0.001 mm to 0.020 mm. It is more preferable that the thickness be 0.001 mm to 0.010 mm.

The outer layer 92 is formed on the inner layer 91. The resin material of the outer layer 92 is not particularly limited, but for example, it is preferable to use a fluorine-based resin material, for example, polytetrafluoroethylene (PTFE), fluoride ethylene propylene (FEP) and the like.

The thickness of the outer layer 92 is not particularly limited, but for example, it is preferable that the thickness be 0.001 mm to 0.030 mm. It is more preferable that the thickness be 0.001 mm to 0.015 mm.

A linear body 93 is formed on the outer layer 92. The linear body 93 is wound in a spiral shape (refer to FIG. 1). In this manner, the linear body 93 is disposed around substantially an entire periphery of the second wire 22. In addition, the linear body 93 is coarsely wound so that the adjacent wires are separate from each other. In the present embodiment, the number of formed linear bodies 93 is one or more. When the number of formed linear bodies 93 is two or more, spirally winding directions of the respective linear bodies 93 may be the same as each other, or may be opposite to each other.

Providing the linear body 93 allows the second wire 22 (wire body 2) to have a plurality of convex portions 94 defined by the linear body 93 on the outer surface thereof and a concave portion 95 formed between the adjacent convex portions 94 (linear bodies 93).

The resin material in the linear body 93 is not particularly limited, but for example, it is preferable to use a fluorine-based resin material, such as polytetrafluoroethylene (PTFE), fluoride ethylene propylene (FEP) and the like.

In the guide wire 1, the friction coefficient in the convex portion 94 (linear body 93) is smaller than the frictional coefficient in a bottom 951 (exposed portion of the outer layer 92) of the concave portion 95.

The cylindrical member 7 is configured to have a cylindrical (ring) shape and is fixedly arranged in the constant outer diameter portion 212 of the wire body 2 (first wire 22). In addition, the cylindrical member 7 is disposed so as to protrude outward from the wire body 2.

An inner diameter $\phi d1$ of the cylindrical member 7 is substantially the same in an axial direction of the wire body 2, and an outer diameter is substantially the same except for a tapered portion 72 to be described later.

The inner diameter $\phi d1$ of the cylindrical member 7 is slightly larger than an outer diameter $\phi d2$ of the constant outer diameter portion 212. That is, a relationship of $\phi d1 > \phi d2$ is satisfied, and a gap S is formed between the inner peripheral surface of the cylindrical member 7 and the outer peripheral surface of the constant outer diameter portion 212. The joint member 8 which joins the cylindrical member 7 to the wire body 2 is formed in the gap S. A thickness D of the gap S is not particularly limited, but it is preferable that the thickness D be approximately 5 μm to 30 μm. By adopting the thickness D of the gap S as described above, the joint member 8 is likely to enter the gap S.

By satisfying the relationship of $\phi d1 > \phi d2$, the cylindrical member 7 is movable with respect to the wire body 2 in a state where the joint member 8 is not disposed. Therefore, a manufacturing method to be described later enables the guide wire 1 to be manufactured simply.

A distal end 71 of the cylindrical member 7 is in contact with the resin coating layer 6, and the proximal end 63 of the resin coating layer 6 is inserted into the inner side (gap S) of the cylindrical member 7. In other words, the distal end 71 of the cylindrical member 7 is positioned at the further distal side than the proximal end 63 of the resin coating layer 6. Therefore, the proximal end 63 of the resin coating layer 6 is not exposed on the surface of the guide wire 1 (does not face outward from the guide wire 1).

An outer diameter (maximum outer diameter) $\phi d3$ of the cylindrical member 7 is larger than an outer diameter $\phi d4$ of a portion of the resin coating layer 6 where the distal end 71 of the cylindrical member 7 is positioned. This cylindrical member 7 causes the proximal end 63 of the resin coating layer 6 to be positioned further inside than the outer peripheral surface of the cylindrical member 7.

The outer diameter $\phi d3$ of the cylindrical member 7 is substantially the same as an outer diameter $\phi d5$ in the vicinity of the proximal portion of the resin coating layer 6. The length of the cylindrical member 7 is shorter than the length of the resin coating layer 6. Since there is a relationship of small and large sizes, for example, when the guide wire 1 moves inside the living body lumen, the resin coating layer 6 having a better sliding property in the distal portion thereof comes into contact with a wall portion defining the living body lumen, earlier than the cylindrical member 7. This enables the guide wire 1 to be operated without degrading the operability.

In the present embodiment, the outer diameter $\phi d5$ in the vicinity of the proximal portion is substantially equal to the maximum outer diameter of the resin coating layer 6. In addition, for example, the "vicinity of the proximal portion" can be a boundary portion between the tapered portion whose outer diameter gradually increases toward the distal side starting from the proximal of the resin coating layer 6 and the constant outer diameter portion which is positioned at the distal side of the tapered portion and whose outer diameter is constant.

The proximal portion of the cylindrical member 7 is configured to have the tapered portion (gradually decreasing outer diameter portion) 72 whose outer diameter gradually decreases toward the proximal direction. By providing the tapered portion 72, it is possible for the rigidity (flexural rigidity, torsional rigidity) of the wire body 2 including the cylindrical member 7 to gradually change toward the distal side of the wire body 2. In addition, it is possible to further minimize a difference in the rigidity between the distal side and the proximal side based on a boundary from the proximal of the cylindrical member 7. As a result, it is possible to improve the ability of the guide wire 1 to follow the blood vessels, and it is also possible to prevent the guide wire 1 from being bent.

In the present embodiment, a tapering angle of the tapered portion 72 is substantially constant along the longitudinal direction. This enables the guide wire 1 to gradually change in rigidity along the longitudinal direction. Unlike in the above-described configuration, the tapering angle of the tapered portion 72 may change along the longitudinal direction, and for example, may be formed by alternately repeating a relatively large tapering angle portion and a relatively small tapering angle portion multiple times. In this case, some portions of the tapered portion 72 may be formed so that the tapering angle is zero degrees.

In an alternative embodiment, the cylindrical member 7 does not have the proximal portion configured to have the tapered portion 72, and for example, may have a constant outer diameter over the entire region in the longitudinal direction of the cylindrical member 7.

The length of the cylindrical member 7 is not particularly limited, but it is preferable that the length be approximately 0.5 mm to 2 mm. By adopting the above mentioned length, it is possible to set a sufficient length which enables the cylindrical member 7 to perform its function while degradation in the operability of the guide wire 1 which is caused by the excessively lengthened cylindrical member 7 is prevented. Specifically, a section S11 where the cylindrical member 7 of the wire body 2 is disposed has rigidity higher than those of a section S12 of the distal side thereof and a section S13 of the proximal side thereof. Accordingly, the section S11 is unlikely to be curved and deformed as compared to the section S12 and the section S13. If the section S11 which is unlikely to be curved is long, there is a possibility that the operability (in particular, the ability to follow) of the guide wire 1 may be degraded. Therefore, by arranging the cylindrical member 7 to have the above-described length and shortening as much as possible the section S11 which is unlikely to be curved and deformed, it is possible to effectively suppress the above-described degradation in the operability.

It is preferable that the cylindrical member 7 have a material harder than the resin material of the resin coating layer 6, and it is preferable to use a metal material as the material of the cylindrical member 7. For example, the metal material can include stainless steel, super-elastic alloys, cobalt-based alloys, and precious metals such as gold, platinum, tungsten and the like, or alloys containing these materials (for example, platinum-iridium alloy). In particular, it is preferable to use a platinum-iridium alloy in view of the hardness and the processing workability of such alloys.

The outer peripheral surface of the cylindrical member 7 (outer peripheral surface of the tapered portion 72) as described above is configured to have a surface continuous with a base portion 81 to be described later of the joint member 8.

The joint member 8 is first used to join (fix) the cylindrical member 7 to the wire body 2. As described above, the inner diameter $\phi d1$ of the cylindrical member 7 is slightly larger than the outer diameter $\phi d2$ of the constant outer diameter portion 212 of the wire body 2. Accordingly, the cylindrical member 7 is movable with respect to the wire body 2 in a state where the joint member 8 is not disposed. Therefore, the joint member 8 is used to fix the cylindrical member 7 to the wire body 2.

The joint member 8 has the base portion 81 positioned at the proximal side of the cylindrical member 7 and an extension portion 82 which extends from the base portion 81 and is inserted into the gap S. The base portion 81 is formed so as to come into contact with a proximal surface 721 of the cylindrical member 7 and the outer surface of the wire body 2. In this manner, the cylindrical member 7 is firmly joined to the wire body 2. The length of the base portion 81 is not particularly limited, but it is preferable that the length be approximately 0.5 mm to 2.0 mm.

On the other hand, the extension portion 82 extends from the base portion 81 and fills the proximal portion of the gap S. That is, the extension portion 82 is formed between the inner peripheral surface of the proximal portion of the cylindrical member 7 and the outer peripheral surface of the wire body 2. In this manner, the cylindrical member 7 is joined to the wire body 2.

By disposing the base portion 81 and the extension portion 82 in this manner, a contact area is widened between the cylindrical member 7 and the wire body 2 via the joint member 8. Therefore, it is possible to more firmly join the cylindrical member 7 to the wire body 2.

Furthermore, the base portion 81 also functions as a step filling member which fills a step between the wire body 2 and the proximal portion (tapered portion 72) of the cylindrical member 7. Specifically, the base portion 81 is positioned at the proximal side of the cylindrical member 7, and has a tapered shape whose outer diameter gradually decreases toward the proximal direction. That is, the base portion 81 defines a tapered portion (gradually decreasing outer diameter portion) whose outer diameter gradually decreases toward the proximal direction. Furthermore, the base portion 81 has a surface which smoothly transitions from the outer peripheral surface of the wire body 2 to the tapered portion.

Therefore, the distal of the catheter can be smoothly guided from the outer surface of the wire body 2 to the cylindrical member 7 via the outer peripheral surface of the base portion 81. As described above, the step between the wire body 2 and the cylindrical member 7 is filled with the base portion 81. In this manner, it is possible to prevent the catheter from being caught thereon. In addition, by providing for the base portion 81 to have the tapered shape, it is possible for the rigidity of the wire body 2 including the base portion 81 to gradually change toward the distal side of the wire body 2.

In particular, in the present embodiment, the tapering angle of the base portion 81 is substantially equal to the tapering angle of the proximal portion (tapered portion 72) of the cylindrical member 7, and the outer peripheral surface of the base portion 81 is configured to have a surface continuous with the outer peripheral surface of the tapered portion 72 of the cylindrical member 7. That is, regions in the vicinity of the proximal side and in the vicinity of the distal side are configured to have a flat surface having no step across the boundary between the base portion 81 and the cylindrical member 7. Therefore, it is possible to effectively prevent the distal of the catheter from being caught on the boundary between the base portion 81 and the cylindrical member 7.

It is preferable that the joint member 8 be made from a material softer than that of the cylindrical member 7 (i.e., a material having a low Young's modulus). For example, it is possible to use various adhesives or solder as the material thereof. Out of the materials, it is preferable to use a solder which is relatively hard, so that the joint member 8 has high mechanical strength, and in a manufacturing method to be described later, it is possible to more simply form the joint member 8. In this manner, if the joint member 8 is configured to have a material softer than that of the cylindrical member 7, it is possible for the rigidity of the wire body 2 including the joint member 8 and the cylindrical member 7 to gradually change toward the distal side of the wire body 2.

The joint member 8 may be made from a material harder than that of the cylindrical member 7 (i.e., a material having a high Young's modulus). In this case, the joint member 8 (in particular, the extension portion 82) also functions as a reinforcement member which reinforces the cylindrical member 7. Therefore, for example, it is possible to lighten the cylindrical member 7.

In the guide wire 1 as described above, the resin coating layer 6, the cylindrical member 7 and the outer surface of the joint member 8 are covered with a hydrophilic lubricant resin layer not illustrated. By being covered with the hydrophilic lubricant resin layer, it is possible to further prevent the distal end of the catheter from being caught thereon. The hydrophilic lubricant resin layer may be disposed on the outer surface of the first wire 21 by being further extended from the joint member 8. In this manner, even if there is a slight step in the boundary portion between the joint member 8 and the first wire 21, since the step is covered with the hydrophilic lubricant resin layer, it is possible to improve the sliding property and thus it is possible to reliably prevent the aforementioned case of being caught thereon.

Next, a manufacturing method of the guide wire 1 will be briefly described.

First, as illustrated in FIG. 3(*a*), the first wire 21 in which the coil 4 and the resin coating layer 6 are formed is prepared.

Next, as illustrated in FIG. 3(*b*), the cylindrical member 7 is disposed onto the first wire 21 from the proximal side of the first wire 21 to thereby encircle a portion of the first wire 21 and the distal of the cylindrical member 7 is attached to the resin coating layer 6. This causes the proximal end 63 of the resin coating layer 6 to be in a state of being inserted into the gap S. In this stage, the outer diameter of the cylindrical member 7 is constant in the longitudinal direction. That is, in this stage, the proximal portion of the cylindrical member 7 is not configured to have the tapered portion 62.

Next, as illustrated in FIG. 3(*c*), melted solder 5 is supplied and solidified so as to fill the step between the first wire 21 and the proximal end of the cylindrical member 7. At this time, a portion of the solder 5 in a melted state flows into the gap S toward the distal side in a capillary inflow manner (by capillary effects). The remaining portion stays at the proximal side of the cylindrical member 7 and is cured. In this state, the remaining portion is protruded further than the cylindrical member 7 so as to cover the outer peripheral surface of the wire body 2 and the outer peripheral surface of the proximal portion of the cylindrical member 7. In an embodiment, in a previous step, a portion where the outer peripheral surface of the first wire 21 is overlapped with the cylindrical member 7 is processed so that wettability (i.e., degree of spread on the surface) of the solder (or adhesive) is higher than that of the other portions Next, as illustrated in FIG. 3(*d*), an extraneous portion is removed from the proximal portion of the cylindrical member 7 and a portion of the solder 5 protruded from the cylindrical member 7, and the proximal portion of the cylindrical member 7 and the portion of the solder 5 protruded from the cylindrical member 7 are formed in a tapered shape. This causes the proximal portion of the cylindrical member 7 to become the tapered portion 62 and forms the base portion 81 having a tapered shape. In addition, according to this method, it is possible to simultaneously and integrally form the tapered portion 72 and the base portion 81. Therefore, it is possible to configure the tapered portion 72 and the base portion 81 so as to have a continuous surface, and thus it is possible to effectively prevent occurrence of a step therebetween. A removal method of the extraneous portion is not particularly limited, but for example, includes a cutting-off method using a file.

Next, the first wire 21 and the second wire 22 are joined together, for example, by welding. This enables the guide wire 1 to be obtained.

Hitherto, the illustrated embodiment of the guide wire has been described. However, the present invention is not limited thereto, and the respective elements of the guide wire can be replaced with any element which can perform the same function. In addition, any element may be added thereto.

In the aforementioned embodiment, a case has been described in which the wire body is prepared by joining two wires together. However, the wire body may be configured as one wire.

In the aforementioned embodiment, a case has been described in which the cylindrical member is a circular tube type. However, for example, the cylindrical member may have a shape in which a slit for internally and externally communicating is formed in the entire region in the longitudinal direction thereof, that is, a C-shape in horizontal cross section.

It is possible to reliably prevent a medical device such as a catheter used in combination with the a guide wire according to this application from being caught on a turned-up portion when the proximal side portion of the coating layer is turned up. Therefore, the guide wire has industrial applicability.

The detailed description above describes a guide wire disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
   an elongated wire body having flexibility;
   a distal side coating layer that covers a distal portion of the wire body and is made of a resin material;
   a cylindrical member that has an outer diameter substantially the same as an outer diameter of a proximal portion of the distal side coating layer, that encircles a portion of the wire body and that has a distal portion positioned proximate the proximal portion of the distal side coating layer; and a joint member that is disposed at a proximal side of the cylindrical member and joins the cylindrical member and the wire body, wherein the joint member has a gradually decreasing outer diameter portion whose outer peripheral surface has a diameter which gradually decreases toward a proximal side of the wire body, wherein a proximal portion of the cylindrical member has a gradually decreasing outer diameter portion whose outer peripheral surface has a diameter which gradually decreases toward the proximal side of the wire body, and wherein the outer peripheral surface of the gradually decreasing outer diameter portion of the proximal portion is continuous with the outer peripheral surface of the gradually decreasing outer diameter portion of the joint member at respective parts of the outer peripheral surfaces whose diameters decrease at a same rate.

2. The guide wire according to claim 1,
wherein the joint member is made of a material softer than a material of the cylindrical member.

3. The guide wire according to claim 1,
wherein a distal end of the cylindrical member is in contact with the proximal portion of the distal side coating layer.

4. The guide wire according to claim 1,
wherein the joint member is inserted from the proximal side of the cylindrical member into a portion between an outer peripheral surface of the wire body and an inner peripheral surface of the cylindrical member.

5. The guide wire according to claim 1,
wherein the joint member is made of an adhesive or solder.

6. The guide wire according to claim 1,
wherein the cylindrical member is made of a metal material.

7. The guide wire according to claim 1,
wherein a proximal most portion of the cylindrical member defines a step.

8. A guide wire comprising:
an elongated wire body having flexibility;
a distal side coating layer that covers a distal portion of the wire body and is made of a resin material;
a cylindrical member that has an outer diameter substantially the same as an outer diameter of a proximal portion of the distal side coating layer, that encircles a portion of the wire body and that has a distal portion positioned proximate the proximal portion of the distal side coating layer; and
a joint member that is disposed at a proximal side of the cylindrical member and joins the cylindrical member and the wire body,
wherein the joint member has a gradually decreasing outer diameter portion whose outer peripheral surface has a diameter which gradually decreases toward a proximal side of the wire body,
wherein a proximal portion of the cylindrical member has a gradually decreasing outer diameter portion whose outer peripheral surface has a diameter which gradually decreases toward the proximal side of the wire body, and
wherein a proximal most portion of the cylindrical member defines a step.

9. The guide wire according to claim 8,
wherein the joint member is made of a material softer than a material of the cylindrical member.

10. The guide wire according to claim 8,
wherein a distal end of the cylindrical member is in contact with the proximal portion of the distal side coating layer.

11. The guide wire according to claim 8,
wherein the joint member is inserted from the proximal side of the cylindrical member into a portion between an outer peripheral surface of the wire body and an inner peripheral surface of the cylindrical member.

12. The guide wire according to claim 8,
wherein the joint member is made of an adhesive or solder.

13. The guide wire according to claim 8,
wherein the cylindrical member is made of a metal material.

* * * * *